(12) United States Patent
Simmons et al.

(10) Patent No.: US 10,251,903 B2
(45) Date of Patent: Apr. 9, 2019

(54) PROCESS FOR MAKING NUCLEOSIDE PHOSPHORAMIDATE COMPOUNDS

(71) Applicants: MERCK SHARP & DOHME CORP., Rahway, NJ (US); IDENIX Pharmaceuticals LLC, Cambridge, MA (US); Bryon L. Simmons, Hamilton, NJ (US); Kevin R. Campos, Berkeley Heights, NJ (US); Artis Klapars, Edison, NJ (US); Alistair J. Stewart, Wayland, MA (US); Benjamin A. Mayes, Boston, MA (US); Peter E. Maligres, Fanwood, NJ (US); Alan Hyde, Jersey City, NJ (US); Steven Mark Silverman, Jersey City, NY (US); Yong-Li Zhong, Edison, NJ (US); Adel M. Moussa, Burlington, MA (US); Kenneth Baker, Syracuse, NY (US); Kara Van Valkenburg, Syracuse, NY (US)

(72) Inventors: Bryon L. Simmons, Hamilton, NJ (US); Kevin R. Campos, Berkeley Heights, NJ (US); Artis Klapars, Edison, NJ (US); Alistair J. Stewart, Wayland, MA (US); Benjamin A. Mayes, Boston, MA (US); Peter E. Maligres, Fanwood, NJ (US); Alan Hyde, Jersey City, NJ (US); Steven Mark Silverman, Jersey City, NY (US); Yong-Li Zhong, Edison, NJ (US); Adel M. Moussa, Burlington, MA (US); Kenneth Baker, Syracuse, NY (US); Kara Van Valkenburg, Syracuse, NY (US)

(73) Assignees: Merck Sharp & Dohme Corp., Rahway, NJ (US); Idenix Pharmaceuticals LLC, Cambridge, MA (US)

( * ) Notice: Subject to any disclaimer, the term of this patent is extended or adjusted under 35 U.S.C. 154(b) by 0 days.

(21) Appl. No.: 15/519,846

(22) PCT Filed: Oct. 20, 2015

(86) PCT No.: PCT/US2015/056333
§ 371 (c)(1),
(2) Date: Apr. 18, 2017

(87) PCT Pub. No.: WO2016/064797
PCT Pub. Date: Apr. 28, 2016

(65) Prior Publication Data
US 2017/0246198 A1    Aug. 31, 2017

Related U.S. Application Data

(60) Provisional application No. 62/130,834, filed on Mar. 10, 2015, provisional application No. 62/066,049, filed on Oct. 20, 2014.

(51) Int. Cl.
C07H 19/10     (2006.01)
A61K 31/7052   (2006.01)
(Continued)

(52) U.S. Cl.
CPC ........... *A61K 31/7052* (2013.01); *C07H 1/00* (2013.01); *C07H 19/10* (2013.01); *C08K 3/08* (2013.01);
(Continued)

(58) Field of Classification Search
CPC ................................. C07H 1/02; C07H 19/10
See application file for complete search history.

(56) References Cited

U.S. PATENT DOCUMENTS 8,334,270 B2 *  12/2012  Sofia .................... A61K 31/706
                                                    514/43
8,906,880 B2 *  12/2014  Du ....................... A61K 31/706
                                                    514/43
(Continued)

FOREIGN PATENT DOCUMENTS

WO    WO-2011123645 A2 *  10/2011   ............ C07F 7/1856
WO    WO-2011123668 A2 *  10/2011   ............ C07F 7/1856
(Continued)

OTHER PUBLICATIONS

J.H. Poupaert, Drug Design: Basic Principles and Applications, in 2 Encyclopedia of Pharmaceutical Technology 1362-1369 (James Swarbrick ed., 3rd ed., 2007).*
(Continued)

*Primary Examiner* — Alexander R Pagano
(74) *Attorney, Agent, or Firm* — Jeffrey P. Bergman; Catherine D. Fitch

(57) ABSTRACT

The present invention is directed to a process for making Nucleoside Phosphoramidate Compounds of formula (I): which are useful for the treatment and prophylaxis of HCV infection. The present invention is also directed to compounds that are useful as synthetic intermediates for making the compounds of formula (I).

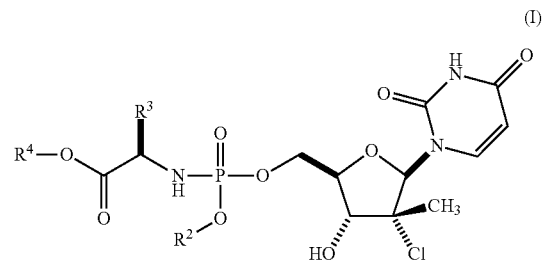

(I)

8 Claims, No Drawings

(51) Int. Cl.
   *C07H 1/00*     (2006.01)
   *C08K 3/08*     (2006.01)

(52) U.S. Cl.
   CPC .............. *C08K 2003/0812* (2013.01); *C08K 2003/0856* (2013.01); *C08K 2003/0893* (2013.01)

(56) References Cited

U.S. PATENT DOCUMENTS

| | | |
|---|---|---|
| 2010/0035835 A1 | 2/2010 | Narjes et al. |
| 2010/0234316 A1 | 9/2010 | MacCoss et al. |
| 2010/0279973 A1 | 11/2010 | Chun et al. |
| 2013/0281686 A1 | 10/2013 | Cho et al. |
| 2014/0271547 A1 | 9/2014 | Dukhan et al. |
| 2014/0286903 A1 | 9/2014 | Chamberlain et al. |
| 2016/0002281 A1* | 1/2016 | Mayes ................... C07H 19/20 514/48 |
| 2016/0083413 A1* | 3/2016 | Gosselin .............. A61K 31/403 424/85.4 |
| 2017/0218006 A1* | 8/2017 | Wilhelm ................ C07H 19/06 |
| 2017/0226146 A1* | 8/2017 | Chung ................... C07H 19/10 |

FOREIGN PATENT DOCUMENTS

| | | |
|---|---|---|
| WO | WO-2013177219 A1 * | 11/2013 .............. C07H 19/20 |
| WO | WO2013177219 A1 | 11/2013 |
| WO | 2014047117 A1 | 3/2014 |
| WO | WO2014058801 A1 | 4/2014 |

OTHER PUBLICATIONS

R. Wilson et al., 71 Journal of Organic Chemistry 8329-8351, 8326 (2006).*

B.S. Ross et al., 76 Journal of Organic Chemistry, 8311-8319 (2011).*

International Search Report and Written Opinion for PCT/US2015/056333, dated Oct. 20, 2015, 10 pages.

* cited by examiner

PROCESS FOR MAKING NUCLEOSIDE PHOSPHORAMIDATE COMPOUNDS

CROSS REFERENCE TO RELATED APPLICATIONS

This application is the national stage application under 35 U.S.C. § 371 of International Patent Application No. PCT/US2015/056333 filed Oct. 20, 2015, which claims priority from U.S. Provisional Patent Application No. 62/130,834, filed Mar. 10, 2015 and U.S. Provisional Patent Application No. 62/066,049, filed Oct. 20, 2014. Each of the aforementioned applications is incorporated by reference in its entirety.

FIELD OF THE INVENTION

The present invention is directed to a process for making Nucleoside Phosphoramidate Compounds which are useful for the treatment or prophylaxis of HCV infection. The present invention is also directed to compounds that are useful as synthetic intermediates in the process of the invention.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, sexually or vertically from infected mothers or carrier mothers to their off-spring.

Inhibition of HCV NS5B polymerase prevents formation of the double-stranded HCV RNA and therefore constitutes an attractive approach to the development of HCV-specific antiviral therapies.

Various substituted nucleoside compounds are known inhibitors of the HCV NS5B protease enzyme. Included in these nucleosides are nucleoside phosphoramidate compounds which are useful in the treatment of infection by HCV and in the treatment, prophylaxis, or delay in the onset or progression of HCV infection. Representative nucleoside phosphoramidate compounds that are useful for treating HCV infection are described, for example, in International Patent Publication Nos. WO 2013/177219 and WO 2014/058801. Among the compounds disclosed in WO 2013/177219 is (R)-isopropyl 2-(((R)-(((2R,3R,4R,5R)-4-chloro-5-(2,4-dioxo-3,4-dihydropyrimidin-1(2H)-yl)-3-hydroxy-4-methyltetrahydrofuran-2-yl)methoxy)(phenoxy) phosphoryl)amino)propanoate, hereinafter referred to as Compound A. Compound A is a known inhibitor of HCV NS5B polymerase and is useful for the treatment of HCV infection. The structure of Compound A is as follows:

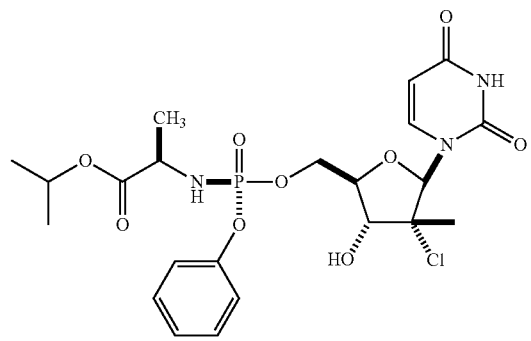

Compound A

International Patent Publication Nos. WO 2013/177219 and WO 2014/058801 disclose methods that can be used to prepare Compound A and related nucleoside HCV NS5B inhibitors. These methods are practical routes for the preparation of Compound A and related nucleoside phosphoramidate compounds.

SUMMARY OF THE INVENTION

The present invention is directed to a process for making Nucleoside Phosphoramidate Compounds of Formula (I) which are useful for the treatment and prophylaxis of HCV infection. More particularly, the present invention includes a method (alternatively referred to herein as "Process A") for preparing a compound of Formula I:

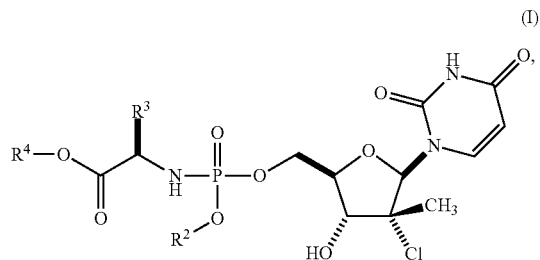

(I)

wherein said process comprising contacting a compound of formula (i):

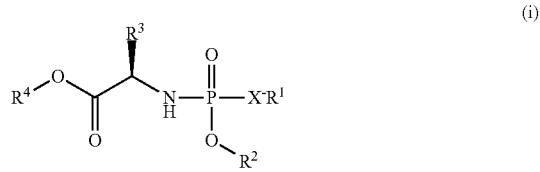

(i)

with a compound of formula (ii):

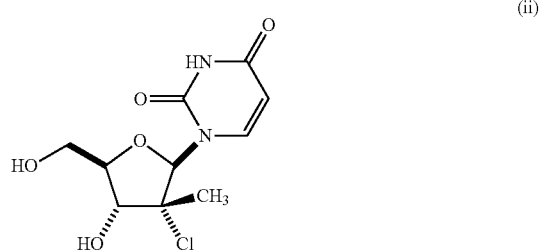

(ii)

in the presence of an aluminum complex, iron complex, zinc complex or magnesium complex and an optional non-nucleophilic base, in an organic solvent A for a time and at a temperature sufficient to form a compound of formula (I), wherein:

X is O, S or NH;

$R^1$ is selected from $C_6$-$C_{10}$ aryl, 5 or 6-membered monocyclic heteroaryl, 9 or 10-membered bicyclic heteroaryl, 5 or 6-membered monocyclic heteroaryl and 4 to 7-membered monocyclic heterocycloalkyl, wherein said 5 or 6-membered monocyclic heteroaryl group, said 9 or 10-membered bicyclic heteroaryl group, said 4 to 7-membered monocyclic heterocycloalkyl group, and said $C_6$-$C_{10}$ aryl group can each be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl and benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —$(C_1$-$C_3$ alkylene$)_m$-$(C_3$-$C_7$ cycloalkyl) and —$(C_1$-$C_3$ alkylene$)_m$-$C_6$-$C_{10}$ aryl);

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently H, $C_1$-$C_6$ alkyl, $C_1$-$C_6$ haloalkyl, $C_1$-$C_6$ hydroxyalkyl, —$(C_1$-$C_3$ alkylene$)_m$-$(C_3$-$C_7$ cycloalkyl), —$(C_1$-$C_3$ alkylene$)_m$-$(C_6$-$C_{10}$ aryl), —$(C_1$-$C_3$ alkylene$)_m$-(4 to 7-membered heterocycloalkyl), —$(C_1$-$C_3$ alkylene$)_m$-(5- or 6-membered monocyclic heteroaryl) or —$(C_1$-$C_3$ alkylene$)_m$-(9- or 10-membered bicyclic heteroaryl); and each occurrence of m is independently 0 or 1;

and wherein organic solvent A is selected from toluene, THF, DCM, MTBE, DMF, propylene carbonate, DME, 1,3-dimethyl-3,4,5,6-tetrahydro-2(1H)-pyrimidinone, 2-methyltetrahydrofuran, xylenes, ethyl acetate, NMP, anisole, isopropyl acetate, acetonitrile and mixtures thereof.

Other embodiments, aspects and features of the present invention are either further described in or will be apparent from the ensuing description, examples, and appended claims.

DETAILED DESCRIPTION OF THE INVENTION

The present invention is directed to a process for making Nucleoside Phosphoramidate Compounds of Formula (I) which are useful for inhibiting HCV NS5B polymerase, inhibiting the replication of HCV and for the treatment or prophylaxis of HCV infection.

Definitions and Abbreviations

The term "alkyl" as used herein, refers to an aliphatic hydrocarbon group, having from 1 to 20 carbon atoms wherein one of its hydrogen atoms is replaced with a bond. An alkyl group may be straight or branched. In one embodiment, an alkyl group has from 1-6 carbon atoms ("$C_1$-$C_6$ alkyl"). In another embodiment, an alkyl group has from 1-4 carbon atoms ("$C_1$-$C_4$ alkyl"). Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. Non-limiting examples of $C_1$-$C_4$ alkyl groups include methyl, ethyl, n-propyl, isopropyl, n-butyl, sec-butyl, isobutyl and tert-butyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms ("C2-C6 alkenyl"). Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "$C_1$-$C_6$ hydroxyalkyl" as used herein, refers to $C_1$-$C_6$ alkyl group, as defined above, wherein one of the $C_1$-$C_6$ alkyl group's hydrogen atoms is replaced with a —OH group. A $C_1$-$C_6$ hydroxyalkyl group may be straight or branched and contain. Non-limiting examples of $C_1$-$C_6$ hydroxyalkyl groups include methanol, ethanol, isopropanol, and tert-butanol.

The term "$C_6$-$C_{10}$ aryl" refers to phenyl and naphthyl. In one embodiment, an aryl group is phenyl. A $C_6$-$C_{10}$ aryl group can be optionally substituted with one or more "ring system substituents" which may be the same or different, and are as defined herein below. In one embodiment, a $C_6$-$C_{10}$ aryl group is unsubstituted.

The term "3 to 7-membered cycloalkyl" refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

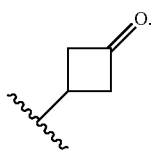

The term "halo" or "halogen" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl and the like, and all isomeric forms thereof. Unless otherwise indicated, a 9 or 10-membered bicyclic heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

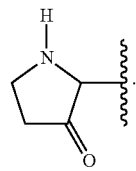 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., m, $R^5$ and $R^6$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds (i), (ii), (II), etc. . . . ), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCV infection.

The term "salt(s)", as employed herein, denotes acidic salts formed with inorganic and/or organic acids, as well as basic salts formed with inorganic and/or organic bases. In addition, when a depicted compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of a compound, starting material or synthetic intermediate of the invention may be formed, for example, by reacting said compound, starting material or synthetic intermediate with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques.

It is also possible that the compounds, starting materials and synthetic intermediates of the invention may exist in different tautomeric forms, and all such forms are embraced within the scope of the invention. For example, all keto-enol and imine-enamine forms of the compounds, starting materials and synthetic intermediates of the invention are included in the invention.

All stereoisomers (for example, geometric isomers, optical isomers and the like) of the present compounds, starting materials and synthetic intermediates of the invention (including those of the salts, solvates, hydrates and esters thereof), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound, starting material or synthetic intermediate of the invention incorporates a double bond or a fused ring, both the cis- and trans-forms, as well as mixtures, are embraced within the scope of the invention.

The following abbreviations are used below and have the following meanings: t-Bu is tertiary butyl, CDI is 1,1'-carbonyldiimidazole; CPME is cyclopentyl methyl ether, DCM is dichloromethane, diglyme is 1-methoxy-2-(2-methoxyethoxy)ethane, DMAC is dimethylacetamide, DME is 1,2-dimethoxyethane, DMF is N,N-dimethylformamide, DMI is 1,3-dimethyl-2-imidazolidinone, EtOAc is ethyl acetate, HPLC is high performance liquid chromatography, IPAC is isopropyl acetate; LC/MS is liquid chromatography/Mass Spectrometry, MTBE is tert-butyl methyl ether, NMP is N-methyl-2-pyrrolidinone, THF is tetrahydrofuran and TLC is thin-layer chromatography.

The Processes of the Present Invention

The present invention is directed to a process for making Nucleoside Phosphoramidate Compounds of Formula (I) which are useful for inhibiting the replication of HCV and for the treatment or prophylaxis of HCV infection. One aspect of the present invention is the process for making Compounds of Formula (I) as set forth above in the Summary of the Invention ("Process A").

In another aspect, the present invention provides synthetic intermediates useful in the processes of the present invention.

In one embodiment, for Process A, the compound of Formula (I) has the formula (I'):

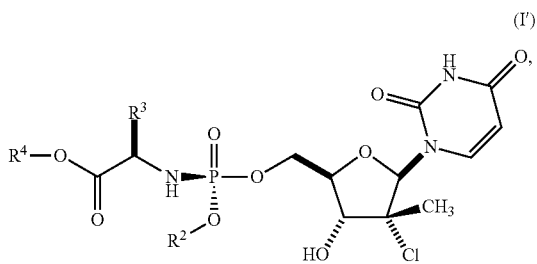

(I')

and the compound of formula (i) has the formula (i'):

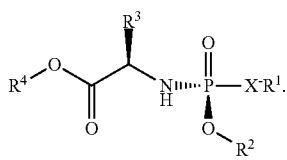

(i')

In another embodiment, for Process A, the compound of Formula (I) has the formula (I"):

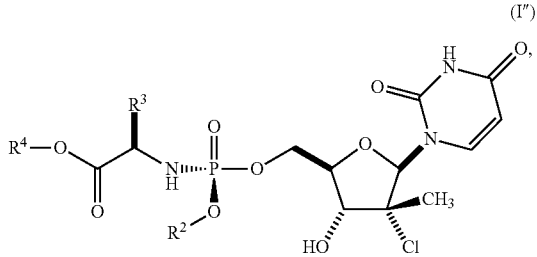

(I")

and the compound of formula (i) has the formula (i"):

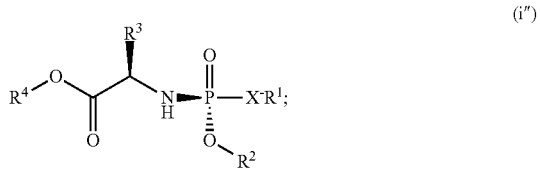

(i")

X is O, S or NH;

$R^1$ is selected from $C_6$-$C_{10}$ aryl, 5 or 6-membered monocyclic heteroaryl, 9 or 10-membered bicyclic heteroaryl, or 4 to 7-membered monocyclic heterocycloalkyl, wherein said 5 or 6-membered monocyclic heteroaryl group, said 9 or 10-membered bicyclic heteroaryl group, said 4 to 7-membered monocyclic heterocycloalkyl group, and said $C_6$-$C_{10}$ aryl group can each be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl or benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —($C_1$-$C_3$ alkylene)$_m$-($C_3$-$C_7$ cycloalkyl) and —($C_1$-$C_3$ alkylene)$_m$-($C_6$-$C_{10}$ aryl);

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl); and each occurrence of m is independently 0 or 1;

and wherein organic solvent A is selected from toluene, THF, DCM, MTBE, DMF, propylene carbonate, DME, 1,3-dimethyl-3,4,5,6-tetrahydro-2(1H)-pyrimidinone, 2-methyltetrahydrofuran, xylenes, ethyl acetate, NMP, anisole, isopropyl acetate, acetonitrile and mixtures thereof.

In one embodiment, for Process A, the process is carried out in the presence of an magnesium complex having the formula ($C_1$-$C_6$ alkyl)MgX or ($C_1$-$C_6$ alkyl)$_2$Mg, wherein X is halo, and wherein the optional base is not present.

In another embodiment, for Process A, the process is carried out in the presence of di-n-butylmganesium or t-butyl magnesium chloride.

In one embodiment, for Process A, the non-nucleophilic base is absent.

In another embodiment, for Process A, the non-nucleophilic base is present.

In another embodiment, for Process A, the non-nucleophilic base is present and is an organic amine.

In one embodiment, for Process A, process is carried out in the presence of an aluminum complex having the formula Al(—O—$C_1$-$C_6$ alkyl)$_3$, ($C_1$-$C_6$ alkyl)$_3$Al, ($C_1$-$C_6$ alkyl)$_2$AlCl or ($C_1$-$C_6$ alkyl)AlCl$_2$ and wherein the optional non-nucleophilic base is present.

In another embodiment, for Process A, the process is carried out in the presence of AlCl$_3$.

In another embodiment, for Process A, the process is carried out in the presence of (CH$_3$)$_2$AlCl.

In still another embodiment, for Process A, the process is carried out in the presence of Al(Ot-Bu)$_3$.

In another embodiment, for Process A, the process is carried out in the presence of AlCl$_3$ in the presence of 2,6-lutidine.

In yet another embodiment, for Process A, the process is carried out in the presence of (CH$_3$)$_2$AlCl in the presence of 2,6-lutidine.

In another embodiment, for Process A, the process is carried out in the presence of Al(Ot-Bu)$_3$ in the presence of 2,6-lutidine.

In another embodiment, for Process A, organic solvent A is THF.

In one embodiment, for Process A, the compound of formula (I) that is made by said process is:

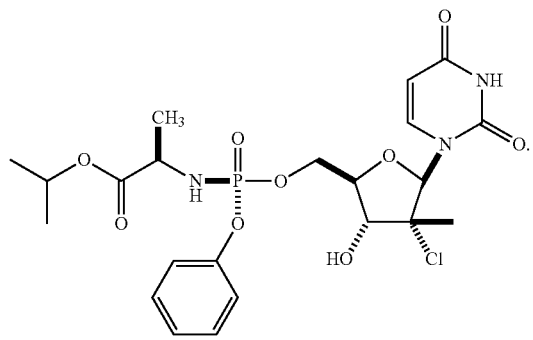

In one aspect, the present invention provides a process for making a compound of formula (i) ("Process B"):

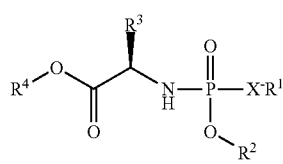

wherein said process comprises the steps:

(A) contacting a compound of Formula (ia):

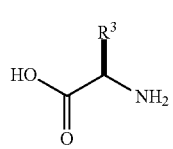

with an acid or a compound of formula ($C_1$-$C_6$ alkyl)$_3$SiCl in an organic alcohol solvent of formula R$^4$OH, for a time and at a temperature sufficient to provide a compound of Formula (ic):

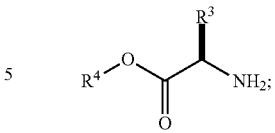

and (B) contacting the compound of formula (ic), or a salt thereof, with a compound of formula (id):

in the presence of a non-nucleophilic base, in an organic solvent B, for a time and at a temperature sufficient to provide an intermediate compound of formula (ie):

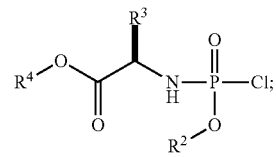

and (C) contacting the compound of formula (ie) with a compound of formula (if):

wherein X is O, S or NH, in the presence of a non-nucleophilic base, in an organic solvent B', for a time and at a temperature sufficient to provide a compound of formula (i'), wherein organic solvents B and B' are each independently selected from an organic acetate, THF, DCM, MTBE, 2-methyltetrahydrofuran, hexanes, xylenes, acetonitrile and mixtures thereof, and wherein:

R$^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more R$^5$ groups;

R$^3$ is selected from $C_1$-$C_6$ alkyl, $C_3$-$C_7$ cycloalkyl, phenyl or benzyl, wherein said $C_3$-$C_7$ cycloalkyl group, said phenyl group and the phenyl moiety of said benzyl group can be optionally substituted with one or more R$^5$ groups;

R$^4$ is selected from $C_1$-$C_6$ alkyl, $C_2$-$C_6$ alkenyl, —($C_1$-$C_3$ alkylene)$_m$-($C_3$-$C_7$ cycloalkyl) and —($C_1$-$C_3$ alkylene)$_m$-($C_6$-$C_{10}$ aryl);

each occurrence of R$^5$ is independently selected from —$C_1$-$C_6$ alkyl, halo, —OR$^6$, —C(O)R$^6$, —CO$_2$R$^6$, —SR$^6$, —$C_1$-$C_6$ hydroxyalkyl, —$C_1$-$C_6$ haloalkyl, —N(R$^6$)$_2$, —S(O)R$^6$, —S(O)$_2$R$^6$, —CN and —NO$_2$;

each occurrence of R$^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl); and each occurrence of m is independently 0 or 1.

In one embodiment, for Process B, step (A) is conducted in the presence of an acid.

In another embodiment, for Process B, step (A) is conducted in the presence of HCl.

In another embodiment, for Process B, step (A) is conducted in the presence of a compound of formula $(C_1-C_6$ alkyl$)_3$SiCl.

In still another embodiment, for Process B, step (A) is conducted in the presence of TMSCl.

In one embodiment, for Process B, the alcohol solvent used in step (A) is isopropanol.

In one embodiment, for Process B, in steps (B) and (C) the non-nucleophilic base used is an organic amine base.

In one embodiment, for Process B, in steps (B) and (C) the non-nucleophilic base used is triethylamine.

In one embodiment, for Process B, organic solvents B and B' are each an organic acetate solvent of the formula $(C_1-C_3$ alkyl)-O—C(O)CH$_3$.

In another embodiment, for Process B, organic solvents B and B' are each isopropyl acetate.

In one embodiment, for Process B, the compound of formula (I) that is made by said process is:

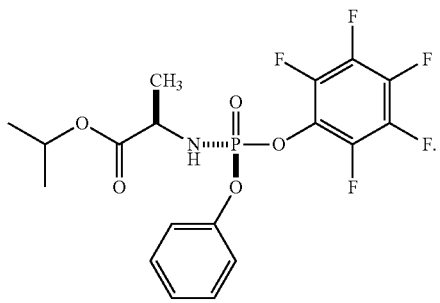

In another embodiment, for Process B, the compound of formula (I) that is made by said process is:

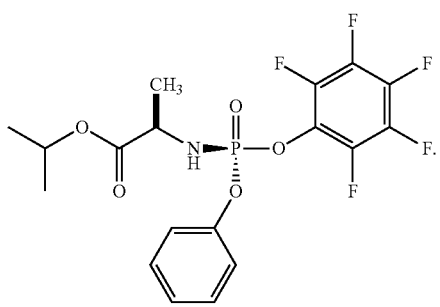 [SMILES: CC(C)OC(=O)[C@@H](C)N[P@](=O)(Oc1ccccc1)Oc1c(F)c(F)c(F)c(F)c1F]

In one aspect, the present invention provides a process for making a compound of formula (i') ("Process C"):

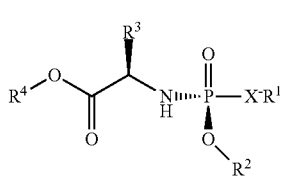

wherein said process comprises taking the reaction mixture obtained in Process B, Step C, and subjecting said reaction mixture to conditions which affect a crystallization-induced dynamic resolution, causing the compound of formula (i') to precipitate out of the reaction mixture, wherein said conditions comprise adding to the reaction mixture obtained in Process B, Step C, an organic solvent B" in which the compound of formula (i') exhibits reduced solubility.

In one embodiment, for Process C, organic solvent B" is selected from an organic hydrocarbon solvents, such as n-heptane and hexanes; an organic ether, such as CPME, MTBE, diethyl ether, or mixtures thereof.

In one aspect, the present invention provides a process for making a compound of formula (i') ("Process D"):

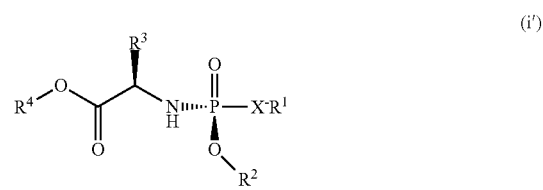

wherein said process comprises taking the reaction mixture obtained in Process B, Step C, and subjecting said reaction mixture to conditions which affect a crystallization-induced dynamic resolution, causing the compound of formula (i') to precipitate out of the reaction mixture, wherein said conditions comprise concentrating the reaction mixture obtained in Process B, Step C.

In one embodiment, for Process D, the reaction mixture obtained in Process B, Step C is concentrated in vacuo.

In one embodiment, for any of Processes A, B, C and D, $R^3$ and $R^4$ are each independently $C_1-C_6$ alkyl.

In another embodiment, for any of Process A, B, C and D, $R^3$ is methyl and $R^4$ is isopropyl.

In one embodiment, for any of Process A, B, C and D, $R^2$ is $C_6-C_{10}$ aryl, which can be optionally substituted as set forth in formula (I).

In another embodiment, for any of Process A, B, C and D, $R^2$ is unsubstituted phenyl.

In one embodiment, for any of Process A, B, C and D, X is O and $R^1$ is a $C_6-C_{10}$ aryl group, optionally substituted with up to 5 groups, each independently selected from $NO_2$ and F.

In another embodiment, for any of Process A, B, C and D, X is O and $R^1$ is pentafluorophenyl.

In another embodiment, for any of Process A, B, C and D, $R^3$ is methyl, $R^4$ is isopropyl and $R^2$ is unsubstituted phenyl.

In still another embodiment, for any of Process A, B, C and D, $R^3$ is methyl; $R^4$ is isopropyl; $R^2$ is unsubstituted phenyl; X is O; and $R^1$ is a $C_6-C_{10}$ aryl group, optionally substituted with up to 5 groups, each independently selected from $NO_2$ and F.

In one aspect, the present invention provides a process for making a compound of formula (ii) ("Process E"):

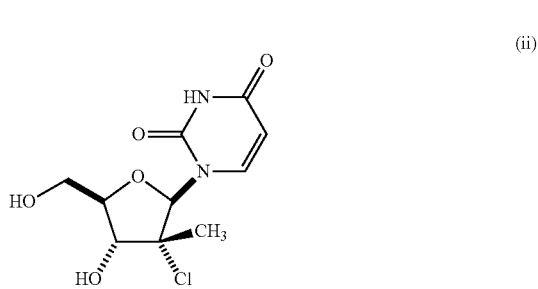

wherein said process comprises the steps:
(A) contacting a compound of Formula (iia):

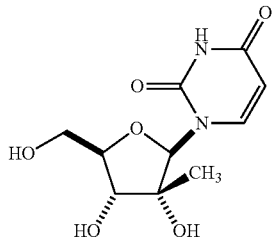

with CDI, in the presence of a base in an organic solvent C, for a time and at a temperature sufficient to provide a compound of Formula (iib):

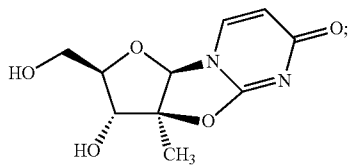

(B) Contacting the compound of formula (iib) with HCl or a compound of formula $(C_1-C_6 \text{ alkyl})_3\text{SiCl}$ to provide a compound of Formula (iic):

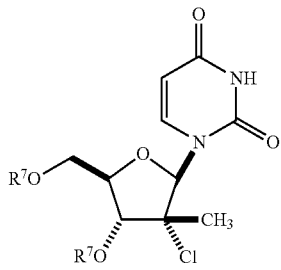

wherein $R^7$ is either H or a hydroxy protecting group;
(C) protecting any free hydroxy groups in the compound of formula (iic) to provide a compound of formula (iid), wherein both $R^7$ groups are a hydroxy protecting group.

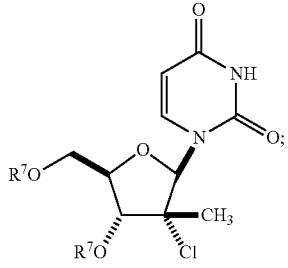

and
(D) contacting the compound of formula (iid) with a base in an organic solvent C' for a time and at a temperature sufficient to provide a compound of Formula (ii), wherein organic solvents C and C' are each independently selected from toluene, DMF, acetic acid, DCM, MTBE, 2-methyl-tetrahydrofuran, xylenes, ethyl acetate, isopropyl acetate, acetonitrile, 1,4-dioxane, DME, THF, CPME and mixtures thereof.

In one embodiment, for Process E, Step A, the base used is an alkali metal hydroxide base.

In one embodiment, for Process E, Step A, the base used is KOH.

In one embodiment, for Process E, Step (B), the compound of formula (iib) is contacted with HCl. $(C_1-C_6\text{alkyl})_3\text{SiCl}$ is $(CH_3)_3\text{SiCl}$.

In another embodiment, for Process E, Step (B), the compound of formula (iib) is contacted with a compound of formula $(C_1-C_6\text{alkyl})_3\text{SiCl}$.

In another embodiment, for Process E, Step (B), the compound of formula (iib) is contacted with $(CH_3)_3\text{SiCl}$.

In another embodiment, for Process E, Step (C), acetic anhydride is used to protect any free hydroxy groups as their acetate ester.

In another embodiment, for Process E, Step (D), the base used is an organic amine base.

In another embodiment, for Process E, Step (D), the base used is triethylamine.

In one embodiment, for Process E, organic solvent C" is DME, DMF or a mixture thereof.

In one embodiment, for Process E, steps (B), (C) and (D) are replaced by the following step (B1):

(B1) contacting the compound of formula (iib) with a compound of formula $(C_1-C_6\text{alkyl})_3\text{SiCl}$ in the presence of organic solvent C" for a time and at a temperature sufficient to provide a compound of Formula (ii), wherein organic solvent C" is selected from DME, DMF, THF, 2-methyl THF, acetonitrile, dimethylacetamide, NMP, CPME, 1,4-dioxane, diglyme, DMI, and mixtures thereof.

In another embodiment, for Process E, Step B1, the compound of formula $(C_1-C_6\text{alkyl})_3\text{SiCl}$ is $(CH_3)_3\text{SiCl}$.

In one embodiment, for Process E, Step B1, organic solvent C" is DME, DMF or a mixture thereof.

The present invention also provides synthetic intermediates useful for making the Compounds of Formula (I).

In one aspect, the present invention provides a compound of formula (III):

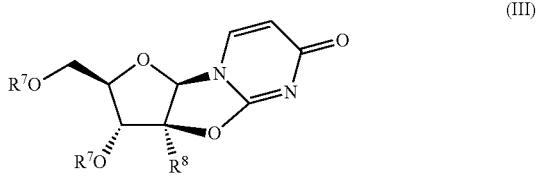

wherein each occurrence of $R^7$ is independently H or a hydroxy protecting group and $R^8$ is $C_1-C_6$ alkyl.

In one embodiment, for the compounds of formula (III), each occurrence of $R^7$ is H.

In another embodiment, for the compounds of formula (III), each occurrence of $R^7$ is a hydroxy protecting group.

In another embodiment, for the compounds of formula (III), each occurrence of $R^7$ is independently H or —C(O)CH$_3$.

In another embodiment, for the compounds of formula (III), each occurrence of $R^7$ is independently H, TMS or pivalate.

In still another embodiment, for the compounds of formula (III), each occurrence of $R^7$ is H.

In another embodiment, for the compounds of formula (III), each occurrence of $R^7$ is —C(O)CH$_3$.

In another embodiment, for the compounds of formula (III), each occurrence of $R^7$ is TMS.

In another embodiment, for the compounds of formula (III), each occurrence of $R^7$ is pivalate.

In one embodiment, for the compounds of formula (III), $R^8$ is methyl.

In another embodiment, for the compounds of formula (III), $R^8$ is methyl and each occurrence of $R^7$ is either H or —C(O)CH$_3$.

In still another embodiment, for the compounds of formula (III), $R^8$ is methyl and each occurrence of $R^7$ is H.

In another embodiment, for the compounds of formula (III), $R^8$ is methyl and each occurrence of $R^7$ is —C(O)CH$_3$.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given.

Example 1

Preparation of Compound 2

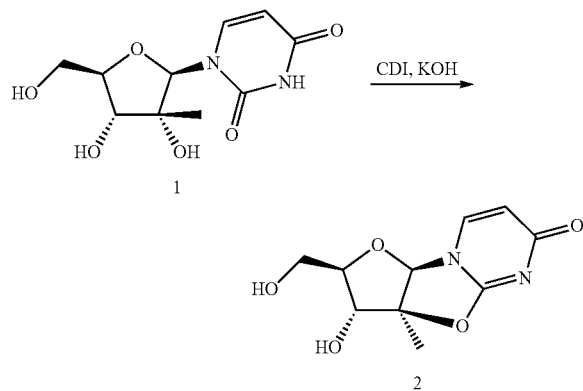

To a flask containing 1.6 L acetonitrile was added Compound 1 (350 g, 1.36 mol, prepared according to the method described in International Patent Publication No. WO 2013/177219), 1,1'-carbonyldiimidazole (212 g, 1.78 mol), and potassium hydroxide (15.3 g, 0.27 mol). The internal reaction temperature was kept below 20° C. during the addition reactants. The resulting reaction was then heated to 80° C. over a 2 hour period, and allowed to stir at this temperature for an additional 18 hours. The reaction mixture was cooled to room temperature, and 700 mL acetonitrile was added. The resulting solution was filtered and the collected solid was dried at 60° C. for 4 hours, then slurried in 1.4 L ethanol for 30 minutes and filtered. The collected solid was dried for about 15 hours at 60° C. to provide the Compound 2 (267.5 g, 99.7% purity by HPLC, 75.3% yield). $^1$H NMR (DMSO-d$_6$, 600.04 MHz): δ 1.59 (s, 3H), 4.01 (m, 1H), 4.24 (m, 1H), 5.03 (brs, 1H), 5.91-5.94 (m, 2H), 6.08 (brs, 1H), 7.86 (d, 1H, J=7.2 Hz).

Example 2

Preparation of Compound 3

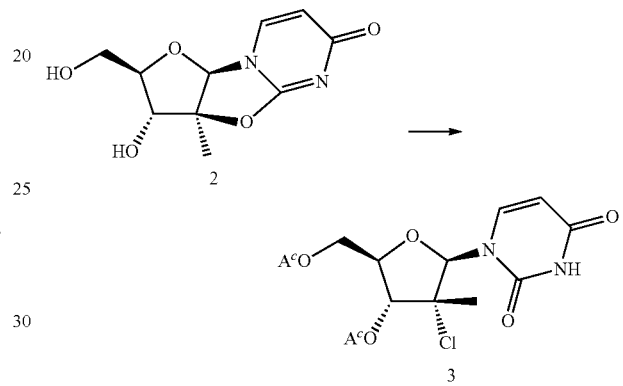

A flask containing 2.2 L dioxane was put under nitrogen atmosphere and the dioxane was cooled to about 10° C. HCl gas was then bubbled into the dioxane (IPC the titration to 8%), after which 430 mL acetic acid was added, followed by Compound 2 (215 g, 0.892 mol). The resulting reaction was heated to 95° C., allowed to stir at this temperature for 8 hours, then cooled to room temperature. The resulting reaction mixture was concentrated in vacuo and the resulting residue was diluted with dichloromethane (970 mL). N,N'-dimethylaminopyridine (21.7 g, 0.18 mol) was then added followed by acetic anhydride (200 g, 1.96 mol), while maintaining solution temperature below 25° C. The resulting reaction was allowed to stir at room temperature for 30 minutes, then methanol (0.856 g, 0.027 mol) was added, followed by 650 mL water and the resulting solution was allowed to stir at room temperature for 30 minutes. The mixture was transferred to a separatory funnel, the layers were separated, and the aqueous layer was back extracted with 650 mL dichloromethane. The combined organic phases were washed with 10% sodium bicarbonate solution (3×1 L) then with saturated aqueous NaCl (1 L). The organic layer was concentrated in vacuo and the resulting residue was diluted with methyl tert-butyl ether (860 mL). The solution was cooled to about 15° C. and allowed to stir at this temperature for 6 hours, then the resulting suspension was filtered. The collected solid was washed with methyl tert-butyl ether (80 mL), and the resulting wet cake was dried at 60° C. for 8 hours to provide compound 3 (250 g, 75% yield, 96.2% purity by HPLC). $^1$H NMR (DMSO-d$_6$, 600.04 MHz): δ 1.50 (s, 3H), δ 2.07 (s, 3H), 2.14 (s, 3H), 4.31-4.37 (m, 3H), 5.25 (brs, 3H), 5.76 (dd, 1H, J=8.4, 2.4 Hz), 6.29 (brs, 1H), 7.75 (d, 1H, J=7.8 Hz), 11.55 (brs, 1H).

Example 3

Preparation of Compound 4

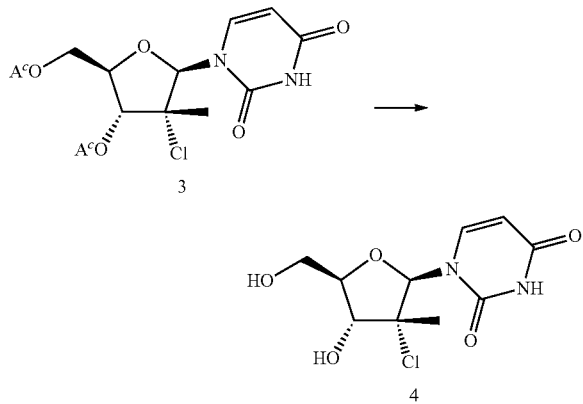

To a flask containing 5 L methanol at room temperature was added compound 3 (1000 g, 2.772 mol) followed by triethylamine (700 g, 6.92 mol). The reaction was allowed to stir at room temperature for 40 hours, then was quenched via addition of acetic acid (416 g, 6.92 mol). The reaction mixture was concentrated in vacuo to 1.5 L, and 2 L of 2-methyltetrahydrofuran was added. The resulting solution was concentrated in vacuo to 1.5 L, then 5 L of 2-methyltetrahydrofuran was added. The resulting mixture was washed with 20% aqueous sodium chloride (5 L), and transferred to a separatory funnel. The layers were separated and the collected aqueous phase was extracted with 2-methyltetrahydrofuran (2×2 L), and the combined organic layers were concentrated in vacuo to a total volume of 1.5 L, while maintaining the temperature below 40° C. Ethyl acetate (2 L) was added to the mixture, and the resulting slurry was cooled to 0° C. and allowed to stir at this temperature for 5 hours. The slurry was filtered and the collected solid was washed with ethyl acetate (1 L). The collected solid was dried at 45° C. for about 15 hours to provide compound 4 (611 g, 99.9% purity by HPLC, 75% yield). $^1$H NMR (DMSO-d$_6$, 600.04 MHz): δ 1.43 (s, 3H), 3.66 (ddd, 1H, J=12.6, 4.8, 2.4 Hz), 3.83-3.89 (m, 2H), 3.92 (dd, 1H, J=9.0, 6.0 Hz), 5.38 (brs, 1H), 5.64 (dd, 1H, J=8.4, 2.4 Hz), 5.92 (d, 1H, J=5.4 Hz), 6.22 (s, 1H), 8.17 (d, 1H, J=8.4 Hz), 11.44 (s, 1H).

Example 4

Alternate Preparation of Compound 4

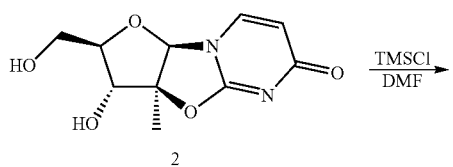

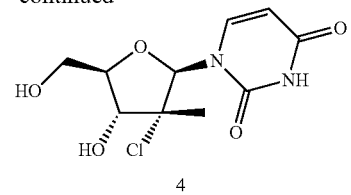

To a 40 mL vial was charged compound 2 (1.88 g as active compound, 7.83 mmol) and DME (20 mL). TMSCl (3.29 mL, 25.1 mmol) was added and the resulting reaction was allowed to stir at room temperature for 10 minutes. DMF (1.21 mL, 15.7 mmol) was added and the resulting mixture was heated to about 90° C. and allowed to stir at this temperature for about 25 hours, then cooled to room temperature. The reaction mixture was filtered and the filtrate was concentrated in vacuo to a total volume of about 5 mL. The resulting solution was diluted with 2-Me-THF (14 mL), then 20% aqueous NaCl solution was added and the resulting biphasic solution was allowed to stir at room temperature for 1 hour. After phase separation, the aqueous layer was back to extracted with 2-Me-THF (2×5 mL). The combined organic layers were azeotropically dried and solvent-switched to IPAc to a total volume of 20 mL. The slurry formed during solvent-switching was allowed to stir at room temperature for about 15 hours, then was cooled to about 5° C. and allowed to stir at this temperature for 20 hours. The mixture was then filtered and the collected crystalline product was rinsed with cold IPAc (8 mL), then dried in vacuo with nitrogen sweep to provide compound 4 (1.85 g, >99% HPLC purity, 85% isolated yield).

Example 5

Preparation of Compound 6

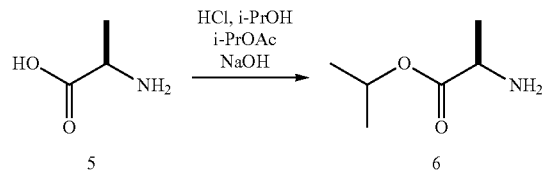

D-alanine (5, 202.33 g, 2.27 mol) and isopropyl alcohol (1000 mL, 5.0 vol) were added to a 1 L reactor and the resulting solution was cooled to 0° C. Hydrogen chloride gas (124.20 g, 3.41 mol, 1.5 equiv) was then added to the reactor over 30 minutes, keeping the internal temperature below 20° C. The reaction was then heated to 70° C. and allowed to stir at this temperature for 20 hours. The reaction was then cooled to room temperature and concentrated via vacuum distillation to a total volume of about 450 mL (2.0-2.5 vol) while maintaining the temperature below 55° C. Isopropyl acetate (1000 mL, 5.0 vol) was added and the resulting solution was concentrated in vacuo to a total volume of about 450 mL (2.0-2.5 vol) while maintaining the batch temperature at 60° C. Isopropyl acetate (600 mL, 3.0 vol) was then added and the resulting solution was cooled to 0° C. and adjusted to pH 7.95 via addition of 4 M NaOH (400 mL, 2.0 vol) while maintaining the solution temperature below 10° C. The solution temperature was then allowed to raise to 25° C., and the adjusted to pH 8.76 via addition of 4 M NaOH (150 mL). The organic layer was isolated. Isopropyl acetate (600 mL, 3.0 vol) was added to the aqueous layer, and the resulting solution was adjusted to pH 10.1 via addition of 4 M NaOH (50 mL). After brief agitation of the resulting basic aqueous solution, the organic layer was removed, and the aqueous layer was extracted with isopropyl acetate (600 mL, 3.0 vol). The three organic layers isolated during workup were combined and concentrated in vacuo to a total volume of about 800 mL (4.0 vol) while maintaining the solution temperature at about 40° C. The final solution had a mass of 733.35 g and contained 30.1 wt % of compound 6 (220.7 g, 74%, 98.6% purity). Final solution water content was 2414 ppm. $^1$H NMR (CDCl$_3$, 500 MHz): δ 1.24 (d, 3H, J=6.3 Hz), 1.25 (d, 3H, J=6.3 Hz), 1.31 (d, 3H, J=7.0 Hz), 1.58 (s, 2H), 3.49 (quartet, 1H, J=7.0 Hz), 5.02 (septet, 1H, J=6.3 Hz).

Example 6

Alternate Preparation of Compound 6

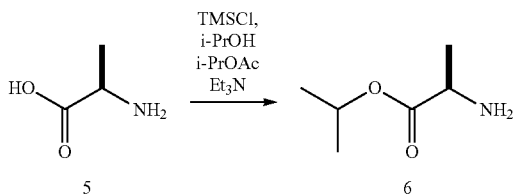

A 2 L round bottom flask was charged with 2-propanol (0.5 L, 6.49 mol) (KF=12) and (R)-2-aminopropanoic acid (5, 89 g, 1 mol). To the resulting solution was added TMSCl (0.191 L, 1.500 mol) over a 10 minute period. The resulting slurry was heated to about 75° C. and the resulting solution was distilled at 550-560 torr to remove about 270 mL of solvent. The resulting mixture was solvent-switched to IPAc while maintaining a constant residual volume by gradually adding a total of 1400 mL IPAc while distilling off 1400 mL at 550-560 torr at about 75° C. The resulting mixture was cooled to 55° C. and triethylamine (TEA, 0.167 L, 1.200 mol) was added. The resulting mixture was seeded with the crystalline triethylamine-HCl salt of compound 6 (0.1 g total) in two equal portions before addition and after 10 mL TEA addition with a 10 minute age at 55° C. to condition the seed bed. The remainder of the addition was conducted over 1 hour at 55° C. The slurry was cooled to 15° C. over a 1 hour period and the cooled slurry was then filtered. The filter cake was washed with 350 mL IPAc and the filtrate was concentrated in vacuo to provide a final IPAc solution of 405 mL, containing 30.8 wt % of compound 6 (115.0 g, 0.876 mol, 88% yield). Characterization data was consistent with that reported above in Example 5.

Example 7

Preparation of Compound 7

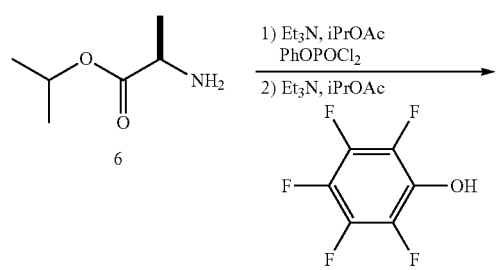

-continued

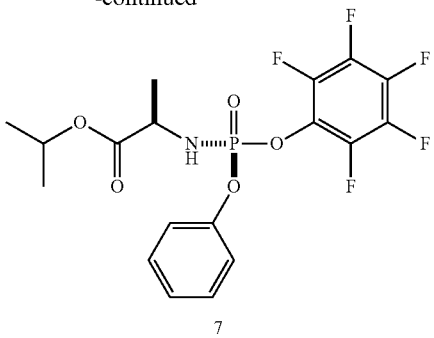

To compound 6 in isopropyl acetate (100 g, 30.1 wt %, 0.23 mol) was added triethylamine (25.4 g, 0.25 mol, 1.1 equiv) to form a first solution. In a separate flask was a second solution of phenyl dichlorophosphate (34.2 mL, 0.23 mol) and isopropyl acetate (240 mL, 8 vol) that was cooled to −5° C. The first solution of compound 6 in isopropyl acetate and triethylamine was added to the second solution of phenyl dichlorophosphate (34.2 mL, 0.23 mol) and isopropyl acetate, and the resulting reaction was warmed to 20° C. and allowed to stir at this temperature for 16 hours. The reaction mixture was filtered, and the collected solid was rinsed with isopropyl acetate (180 mL, 6 vol). The filtrate and wash were combined and cooled to 0° C., and a solution of pentafluorophenol (50.52 g, 0.27 mol, 1.2 equiv) and triethylamine (27.77 g, 0.27 mol, 1.2 equiv) in isopropyl acetate (113 mL) was added to the combined solutions. The resulting reaction was warmed to 20° C. with stirring then filtered to remove solids. The collected solid was rinsed with IPAC (180 mL, 6.0 vol), and the combined filtrate and wash were combined and seeded with compound 7. The resulting solution was then concentrated in vacuo to a total volume of about 425 mL (13.3-15.0 vol) while maintaining a solution temperature of 25° C. Heptane (400 mL, 13.3 vol) was added and the resulting solution was concentrated via vacuum distillation to ~425 mL (13.3-15.0 vol) while maintaining the solution temperature at 25° C. Heptane (400 mL, 13.3 vol) was added and the resulting solution was cooled to 20±5° C. followed by agitation for about 15 hours. The reaction mixture was then filtered and the collected solid was washed sequentially with heptane (180 mL, slurry), water (180 mL, slurry), heptane (180 mL, slurry), and finally heptane (180 mL, displacement) followed by drying in vacuo at 50° C. (nitrogen bleed) for 3 days to provide compound 7 (61.55 g, 59% yield, 98.8% purity). $^1$H NMR (DMSO-d$_6$, 600.04 MHz): δ 1.15 (d, 3H, J=6.6 Hz), 1.16 (d, 3H, J=6.0 Hz), 1.28 (d, 3H, J=7.2 Hz), 3.93 (m, 1H), 4.87 (hept, 1H, J=6.0 Hz), 6.86 (dd, 1H, J=13.8, 9.6 Hz), 7.21-7.25 (m, 3H), 7.41 (t, 2H, J=7.8 Hz).

Example 8

Preparation of Camphorsulfonic Acid Salt of Compound 6

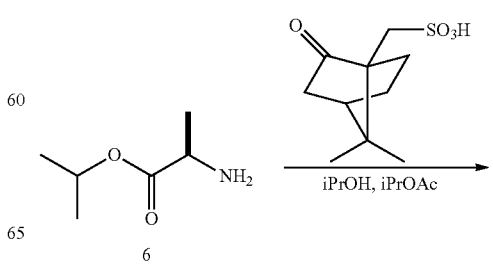

-continued

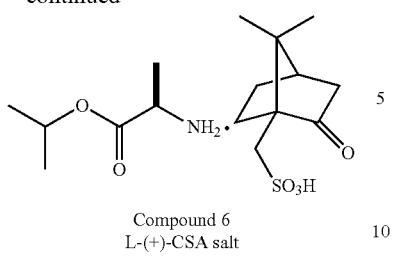

Compound 6
L-(+)-CSA salt

A room temperature solution of (R)-isopropyl 2-aminopropanoate (6, 1.312 g, 10 mmol) in 4 mL of an 1:1 IPA-IPAc mixture was added over a 3 minute period to a 70° C. solution of S(+)-Camphorsulfonic acid (2.323 g, 10 mmol) in 12 mL of a 3:1 IPAc-IPA mixture. The reaction mixture was cooled to 5° C. over 1 hour, then filtered. The collected solid was washed with 15 mL of a 4:1 IPAc-IPA mixture, then washed with 15 mL of IPAc and dried under a nitrogen stream for about 15 hours to provide the L-(+)-CSA salt of compound 6 as a white crystalline solid (3.238 g). The resulting 1:1 salt does not contain solvents, as indicated by NMR analysis. $^1$H NMR (DMSO-$d_6$, 500 MHz): δ 0.75 (s, 3H), 1.05 (s, 3H), 1.23-1.32 (overlapping m, 8H), 1.39 (d, 3H, J=7.2 Hz), 1.81 (d, 1H, J=18.1 Hz), 1.86 (m, 1H), 1.94 (d, 1H, J=9.0 Hz), 2.25 (dt, 1H, J=18.1, 7.8 Hz), 2.40 (d, 1H, J=14.7 Hz), 2.67 (m, 1H), 2.89 (d, 1H, J=14.7 Hz), 4.04 (quartet, 1H, J=7.2 Hz), 4.99 (septet, 1H, J=6.2 Hz), 8.30 (s, 3H).

Example 9

Preparation of Compound A

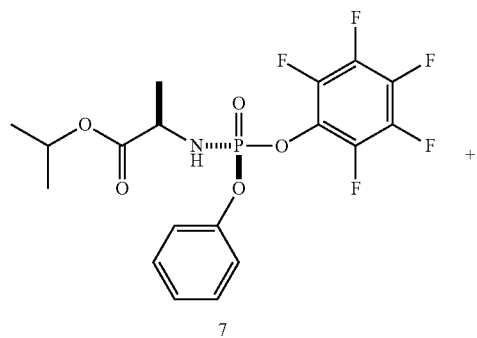

7

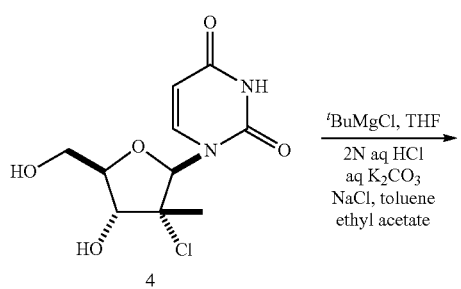

4

-continued

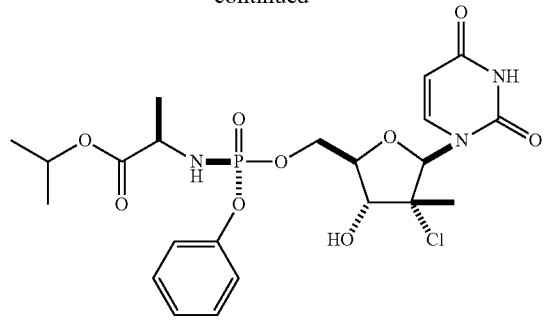

Compound A

Compound 4 (25.5 g, 92.2 mmol, 1.00 eq.), compound 7 (55.0 g, 121 mmol, 1.32 eq.) and THF (590 mL) were added to a 1 L Jacketed reactor. The resulting solution was stirred under nitrogen atmosphere and cooled to −5° C. A solution of tert-butylmagnesium chloride, 1.7 M in THF (90.0 mL, 153 mmol, 1.65 eq.) was slowly added to the reaction mixture over 2.5 hours while the internal reaction temperature was maintained at about −5° C. The reaction mixture was then warmed to 5° C. and allowed to stir at this temperature for about 15 hours. An aqueous solution of 2M HCl (110 mL) was then slowly added to the reaction mixture at <25° C. over 1 hour, then toluene (204 mL) was added. The resulting reaction was allowed to stir at 20° C. for 15 minutes, then the organic layer was separated and was washed with 2M HCl (2×50 mL), then water (50 mL). The organic solution was washed again with 5% K2CO$_3$ aqueous solution (2×50 mL) and 5% NaCl aqueous solution (50 mL). The washes were combined and back-extracted with a toluene (102 mL)/THF (153 mL) solution. The organic layers were combined and concentrated in vacuo to ~250 mL (266 g, 5 vol. of IDX21437-1). To the resulting solution was added ethyl acetate (561 mL) and the resulting solution was filtered to remove inorganic salts. The filtrate was then concentrated in vacuo at 45° C. and recharged with ethyl acetate until a solvent ratio of 80:20 (ethyl acetate:toluene), ~8 volumes (172.18 g) was reached. The reaction mixture was heated to gentle reflux and allowed to stir at this temperature for 2 hours, then the reaction mixture was cooled to 20° C. over a 2 hour period. The reaction mixture was then allowed to stir at 20° C. for and additional 2 hours, then filtered. The collected solid was rinsed with 76 mL of EtOAc and dried in vacuo at 55° C. to provide Compound A. (36 g, 72% yield, 96.4% purity). $^1$H NMR (DMSO-$d_6$, 600.04 MHz): δ 1.13 (d, 3H, J=6.2 Hz), 1.14 (d, 3H, J=6.2 Hz), 1.22 (d, 3H, J=7.1 Hz), 1.40 (s, 3H), 3.78 (m, 1H), 3.84 (brs, 1H), 4.07 (m, 1H), 4.28 (m, 1H), 4.40 (m, 1H), 4.85 (hept, 1H, J=6.2 Hz), 5.57 (dd, 1H, J=8.1, 1.5 Hz), 6.14 (m, 1H), 6.17 (d, 1H, J=5.1 Hz), 6.27 (s, 1H), 7.18 (m, 1H), 7.25 (m, 2H), 7.37 (m, 2H), 7.59 (d, 1H, J=8.1 Hz), 11.52 (s, 1H).

Example 10

Alternate Preparation of Compound A

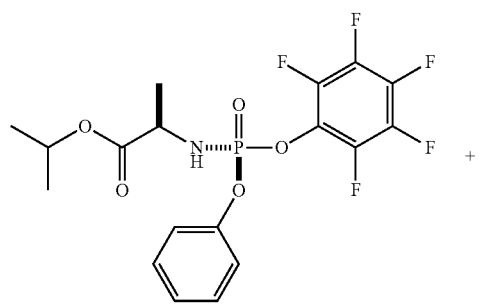

7

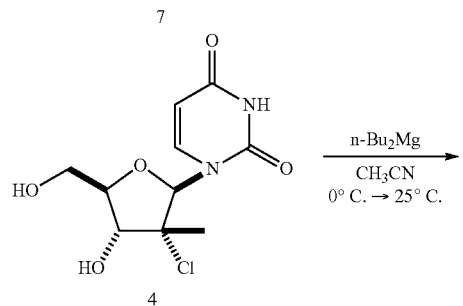

4

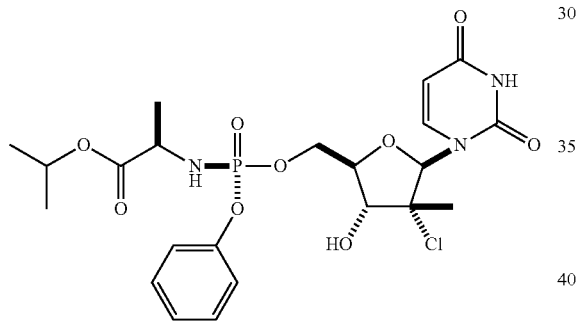

Compound A

Compound 4 (10.0 g, 36.1 mmol, 1.00 eq.), compound 7 (19.6.0 g, 43.3 mmol, 1.20 eq.) and MeCN (200 mL) were added to a 500 mL jacketed reactor. The resulting solution was stirred under nitrogen atmosphere and cooled to −5° C. A solution of di-n-butylmagnesium (1.0 M in heptane (21.7 mL, 21.7 mmol, 0.6 eq.) was added to the reaction mixture over a 20 minute period while maintaining the internal temperature below 5° C. The reaction mixture was warmed to 25° C. and allowed to stir at this temperature for 15 hours, then was warmed to 50° C. and stirred at this temperature for an additional 4 hours. The reaction mixture was then cooled to 0° C. and an aqueous solution of 2M HCl (50 mL) was slowly added to the reaction mixture. The resulting reaction was allowed to stir at 0° C. for 5 minutes, then the organic layer was separated and was washed with 20% aqueous NaCl solution (30 mL). The organic solution was then concentrated in vacuo to a volume of ~50 mL and diluted with 2-methyl THF (160 mL). The resulting solution was washed sequentially with water (30 mL) and 20% NaCl (30 mL). The organic phase was collected, diluted with 2-methyl THF (160 mL) and concentrated in vacuo to a total volume of ~180 mL (KF=2500). Upon concentration, solids precipitated, which were dissolved by heating the mixture to 55° C. The reaction mixture was cooled to 45° C. and seeded with compound A (100 mg) and the resulting solution was allowed to cool to 25° C. over a 3 hour period. Heptane (160 mL) was added to the mixture over 3 hours and the resulting slurry was stirred for 12 hours and then filtered. The isolated solids were rinsed twice with a 1:1 mixture of 2-methyl THF/heptane (40 mL total) and dried in vacuo at 45° C. to provide Compound A. (16.0 g, 78% yield, 96.5% purity). Characterization data was consistent with that reported above in Example 9.

Example 11

Alternate Preparation of Compound A

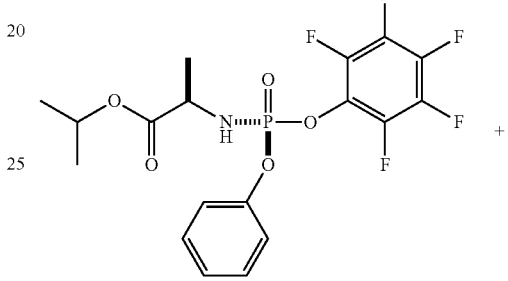

7

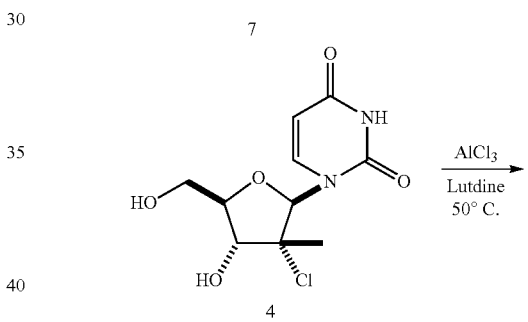

4

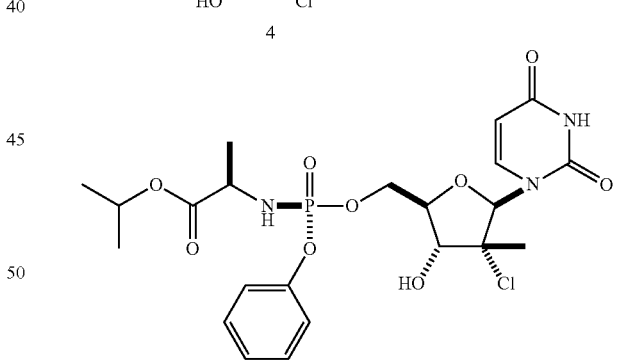

Compound A

A solution of compound 4 (5.00 g, 18.1 mmol) and compound 7 (9.83 g, 21.7 mmol) in THF (100 mL) was cooled in an ice bath to 5° C. and Aluminum chloride (1.21 g, 9.04 mmol) was added in several portions. 2,6-Lutidine (6.31 mL, 54.2 mmol) was added while maintaining the reaction temperature at about 5° C., and the resulting reaction was allowed to stir for 14 hours at 25° C. The reaction temperature was raised to 50° C. and the reaction was allowed to stir at this temperature for 5.5 hours. The reaction mixture was then cooled to 5-10° C. and diluted with 2M aq HCl (25 mL) and iPrOAc (25 mL). The resulting mixture was transferred to a reparatory funnel with an additional 2M aq HCl (25 mL) and iPrOAc (25 mL). The layers were separated and the organic phase was washed sequentially with water (25 mL) and 3% brine (30 mL). The organic phase was concentrated in vacuo using additional iPrOAc (50 mL) to ~⅓ volume. The resulting slurry was stirred at 25° C. and then filtered. The collected solid was washed with iPrOAc (2×20 mL) and dried in a vacuum funnel under a stream of nitrogen to provide Compound A (8.37 g, 85% yield). Characterization data was consistent with that reported above in Example 9.

Example 12

Alternate Preparation of Compound A

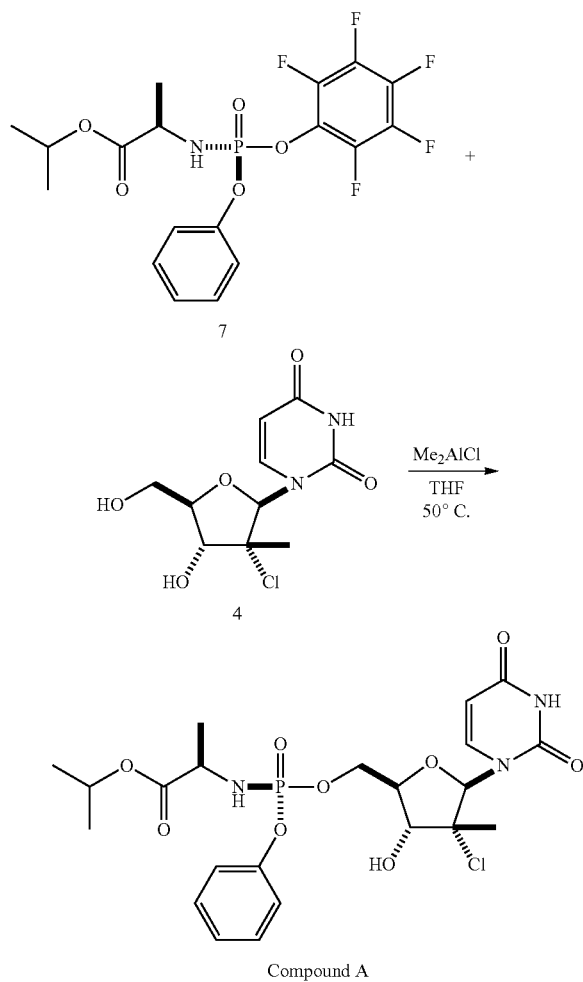

To a 0° C. solution of compound 7 (16 g, 57.8 mmol) and compound 4 (31.5 g, 69.4 mmol) in tetrahydrofuran (240 mL) was added 2,6-dimethylpyridine (10.07 mL, 87 mmol) followed by a 0.75 M solution of dimethylaluminum chloride in n-heptane (38.5 mL, 28.9 mmol). The resulting reaction was allowed to stir at room temperature for about 14 hours, then the reaction was heated to 50° C. and allowed to stir at this temperature for about 7 hours. The reaction mixture was cooled to 20° C. and a solution of L-tartaric acid (81 g, 162 mmol) in water (80 mL) was added, followed by isopropyl acetate (48 mL). The resulting solution was transferred to a separatory funnel and the organic phase was washed with 3% aqueous NaCl solution (80 mL). A 135 g portion of the organic layer (the total weight of the organic layer before subdivision was 281 g) was distilled down to a total volume of 40 mL while feeding in isopropanol (146 mL). After removal of a 5 mL sample from the 40 mL batch, the remaining mixture was warmed to 70° C. and isopropanol (6 mL) was added. After cooling the resulting solution to 55° C. and seeding with compound A (117 mg), n-Heptane (40 mL) was added over 2 hours via syringe pump, while maintaining solution temperature at 55° C. Upon completion of n-heptane addition, the solution was cooled to room temperature over a 3 hour period and then allowed to stir for 1 hour at room temperature. The resulting suspension was wet-milled, annealed for 1 hour at 60° C., then cooled to 0° C. over 3 hours. The resulting suspension was filtered and the collected solid was washed with a 1:1 mixture of isopropanol and n-heptane (3×20 mL) to provide compound A as a solid (9.07 g, 68% yield). Characterization data was consistent with that reported above in Example 9.

Example 13

Alternate Preparation of Compound A

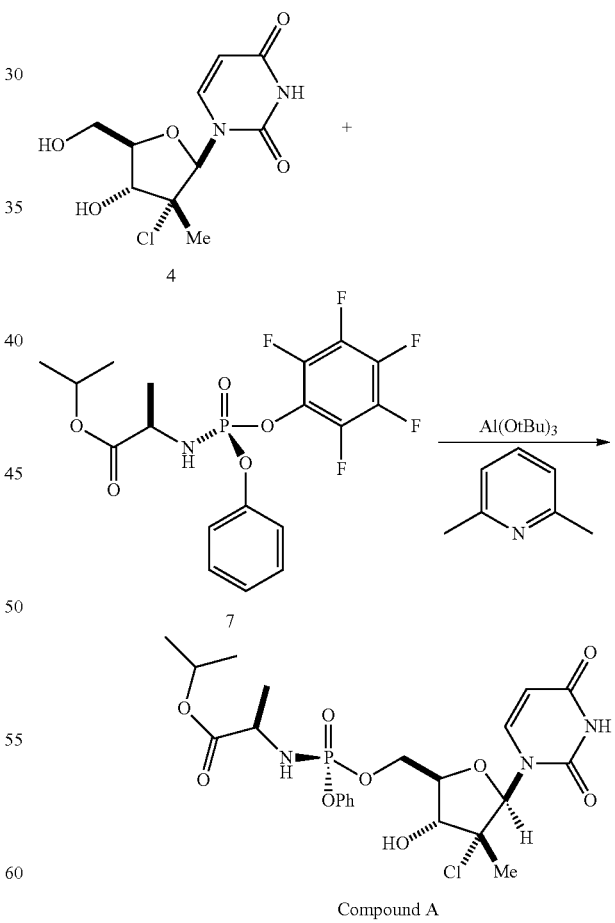

To a 250 mL jacketed flask was added compound 4 (5 g, 18.07 mmol) and compound 7 (10.65 g, 23.49 mmol) followed by addition of THF (65 mL). The resulting solution was cooled to 0° C. and 2,6-dimethylpyridine (3.15 ml, 27.1 mmol) was added slowly. To the resulting mixture was added a solution of Al(OtBu)₃ (2.226 g, 9.04 mmol) in THF (10 mL), during which time the reaction temperature was maintained below 5° C. The reaction mixture was then allowed to warm to 25° C. and allowed to age at this temperature for 18 hours. The reaction was then quenched with 25 mL tartaric acid (30%) and IPAC (25 mL) was added to the quenched reaction mixture. The organic layer was collected and washed with 5% brine (2×75 mL), then concentrated in vacuo and the solvent was switched to IPA (final IPA volume was about 36 mL). The resulting slurry was heated to 70° C. to provide a clear solution which was then cooled to 55° C. and seeded with crystals of Compound A. Heptane (36 mL) was added to the resulting slurry and the slurry was cooled to room temperature and allowed to age for about 15 hours. The slurry was then filtered and the wet filter cake was washed with IPA/Heptane (1:1) and dried under vacuum to provide Compound A as a solid (8.4 g, 85%). Characterization data was consistent with that reported above in Example 9.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for making a compound of Formula (I):

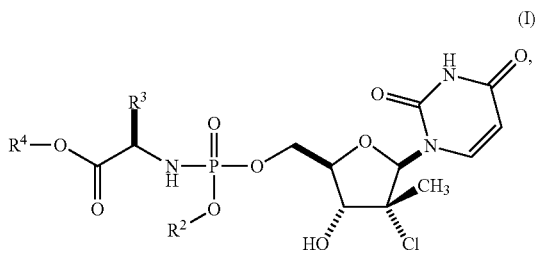

(I)

said process comprising contacting a compound of formula (i):

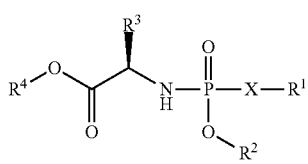

(i)

with a compound of formula (ii):

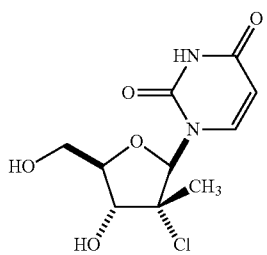

(ii)

in the presence of an aluminum complex, iron complex, or zinc complex, and an optional non-nucleophilic base, in an organic solvent A for a time and at a temperature sufficient to form a compound of formula (I), wherein:

X is O, S or NH;

$R^1$ is selected from $C_6$-$C_{10}$ aryl, 9 or 10-membered bicyclic heteroaryl, and 5 or 6-membered monocyclic heteroaryl, wherein said 5 or 6-membered monocyclic heteroaryl group, said 9 or 10-membered bicyclic heteroaryl group, and said $C_6$-$C_{10}$ aryl group can each be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl and benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —($C_1$-$C_3$ alkylene)$_m$-($C_3$-$C_7$ cycloalkyl) and —($C_1$-$C_3$ alkylene)$_m$-($C_6$-$C_{10}$ aryl);

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently selected from H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl); and each occurrence of m is independently 0 or 1;

and wherein organic solvent A is selected from toluene, THF, DCM, MTBE, DMF, propylene carbonate, DME, 1,3-dimethyl-3,4,5,6-tetrahydro-2(1H)-pyrimidinone, 2-methyltetrahydrofuran, xylenes, ethyl acetate, NMP, anisole, isopropyl acetate, acetonitrile and mixtures thereof.

2. The process of claim 1, wherein the compound of Formula (I) has the formula (I'):

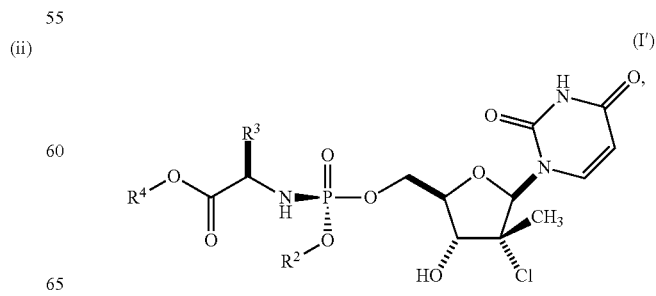

(I')

and the compound of formula (i) has the formula (i'):

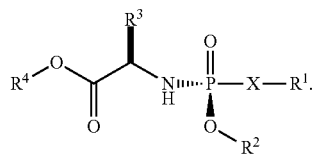
(i')

3. The process of claim 1, wherein the process is carried out in the presence of an aluminum complex having the formula Al(—O—$C_1$-$C_6$ alkyl)$_3$, ($C_1$-$C_6$ alkyl)$_3$Al, ($C_1$-$C_6$ alkyl)$_2$AlCl, ($C_1$-$C_6$ alkyl)AlCl$_2$ or AlCl$_3$, and wherein the optional non-nucleophilic base is present and is an organic amine base.

4. The process of claim 1, wherein X is O and $R^1$ is a $C_6$-$C_{10}$ aryl group, optionally substituted with up to 5 groups, each independently selected from $NO_2$ and F.

5. The process of claim 4, wherein X is O and $R^1$ is pentafluorophenyl.

6. The process of claim 5, wherein $R^3$ is methyl, $R^4$ is isopropyl and $R^2$ is unsubstituted phenyl.

7. The process of claim 1, wherein the compound of formula (I) that is made by said process is:

8. The process of claim 1, wherein the compound of formula (I) that is made by said process is:

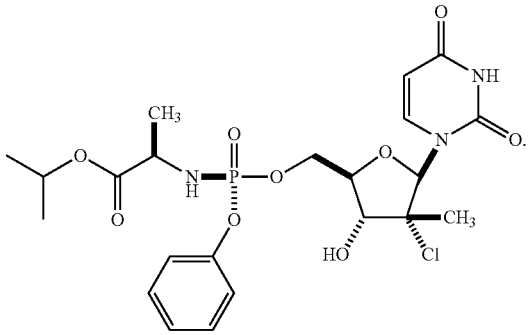 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

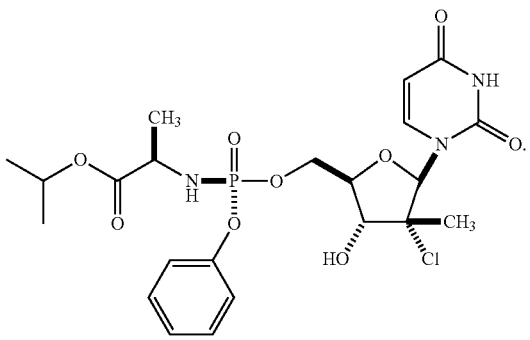 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

* * * * *